350-312
8/16/77    XR    4,042,304    SR

United States Patent [19]
Martin et al.

[11] 4,042,304
[45] Aug. 16, 1977

[54] CHRISTIANSEN EFFECT DETECTOR

[75] Inventors: Archer J. P. Martin, Abbotsbury, Barnet Lane, Elstree, England; James M. Miller, 8 Oxford Lane, Madison, N.J. 07940; Robert J. Mathieu, 249 Morris Avenue, Mountain Lakes, N.J. 07046; Alexander E. Lawson, Jr., 150 Rte. 24, Mendham, N.J. 07945

[73] Assignee: GOW-MAC Instruments, Inc., Madison, N.J.

[21] Appl. No.: 304,096

[22] Filed: Nov. 6, 1972

[51] Int. Cl.² .......................................... G01N 21/46
[52] U.S. Cl. .................. 356/128; 73/61.1 C; 250/574; 350/312; 356/206; 356/246
[58] Field of Search ............... 250/218; 350/267, 312; 356/94, 103, 128, 134, 206; 73/61.1 C

[56] References Cited
U.S. PATENT DOCUMENTS

| | | | |
|---|---|---|---|
| 3,080,746 | 3/1963 | Nerheim | 73/61.1 C |
| 3,416,865 | 12/1968 | Townsend | 356/206 |
| 3,489,906 | 1/1970 | Beer | 250/218 |
| 3,492,396 | 1/1970 | Dalton et al. | 356/39 |
| 3,493,304 | 2/1970 | Rovner | 356/103 |
| 3,499,712 | 3/1970 | Kottle et al. | 356/128 |
| 3,510,271 | 5/1970 | Emneus et al. | 73/61.1 C |
| 3,513,319 | 5/1970 | Broerman | 250/218 |
| 3,530,233 | 9/1970 | Chai et al. | 350/312 |
| 3,564,263 | 2/1971 | Shaw | 356/103 |
| 3,586,417 | 6/1971 | Fields | 350/312 |

OTHER PUBLICATIONS

Strong, J., *Concepts of Classical Optics,* San Francisco, 1958, pp. 583-585.
Clarke, R. H., *A Theory for the Christiansen Filter,* Applied Optics, 7(5), pp. 861-868, May 1968.
Auerbach, L., *Some Simple Christiansen Filters,* American Journal of Physics, 25(7), pp. 440-442, Oct. 1957.
Auerbach, L., *More Christiansen Filters,* American Journal of Physics, 28(8), p. 743, Nov. 1960.
Schrader, W., *Zur Theorie der Dispersionsfilter (Christiansen–Farbfilter),*. Optik, 15(5), May 1958, pp. 265-274.
Matovich, E., *Fast Variable Color Filter,* ISA Journal, Dec. 1965.

*Primary Examiner*—John K. Corbin
*Assistant Examiner*—Conrad Clark
*Attorney, Agent, or Firm*—James W. Hiney, Jr.

[57] ABSTRACT

A detector used in apparatus for measuring variations in the composition of a liquid includes a cell utilizing the Christiansen effect on light transmitted by the liquid flowing through the cell filled with particulate matter. The liquid and the particulate matter have indices of refraction that are substantially equal to one another at a specific wavelength. Variations of the transmitted light can determine changes of the refractive index of the liquid.

Differences in the intensity of light transmitted through a sample cell and a reference device can be determined.

1 Claim, 6 Drawing Figures

CHRISTIANSEN EFFECT DETECTOR

BACKGROUND OF THE INVENTION

The invention is a detector that is more particularly described as a Christiansen effect detector.

In the prior art, there are known methods for using light and the principles of optics for determining differences between two liquids and variations if any of the composition of a liquid. It is known that automatic differential recording systems have been built utilizing photometric means for determining any difference between the refractive indices of two liquids.

These prior systems may be used as detectors in chromatography where a sensitive reading must be made from a sample having a very small volume. The result of the reading must be reproducible when a similar sample is run. Complex prior apparatus, which can provide sufficient sensitivity and can reproduce sample results adequately, is expensive to build.

SUMMARY OF THE INVENTION

Therefore it is an object of the invention to provide an improved optical detection system.

It is also an object to develop an improved liquid chromatography apparatus.

It is a further object to improve the detection apparatus utilized in chromatography.

It is a further object to develop an improved detection apparatus for determining the refractive index of a liquid.

These and other objects of the invention are realized in a detection system utilizing the Christiansen effect on light transmitted by a liquid passing through a cell filled with particulate matter.

It is a feature of the invention to provide a detector utilizing the Christiansen effect on light transmitted by the liquid flowing through the cell filled with particulate matter.

It is another feature to direct a beam of collimated light along a line having a fixed length through the liquid and the particulate matter in the cell.

It is another feature to utilize monochromatic light.

It is still another feature to fill the cell with particles having a refractive index substantially equal to the refractive index of the liquid at a specific wavelength.

It is a further feature to interpose a photodetector in the path of light emerging from the cell for determining the Christiansen effect on light transmitted through the liquid and particulate matter in the cell.

It is a still further feature to determine the intensity of light in a halo resulting from the Christiansen effect.

It is another feature to provide means for flowing the liquid through the cell while the light is being transmitted through the cell.

It is still another feature to detect variations between the intensity of light transmitted by the cell and of light transmitted by a reference device.

It is also a feature to utilize a Christiansen effect detector for determining the refractive index of a liquid.

It is still another feature to provide means for passing a liquid through particulate matter filling reference and sample cells of a fixed length while directing light through that fixed length of the cells to separate photodetectors and to provide means for adding a sample into the sample cell and determining differences in the intensities of light transmitted to the photodetectors.

BRIEF DESCRIPTION OF THE DRAWINGS

A better understanding of the invention may be derived from the detailed description following if that description is considered with respect to the attached drawings wherein.

DETAILED DESCRIPTION

Figure 1:
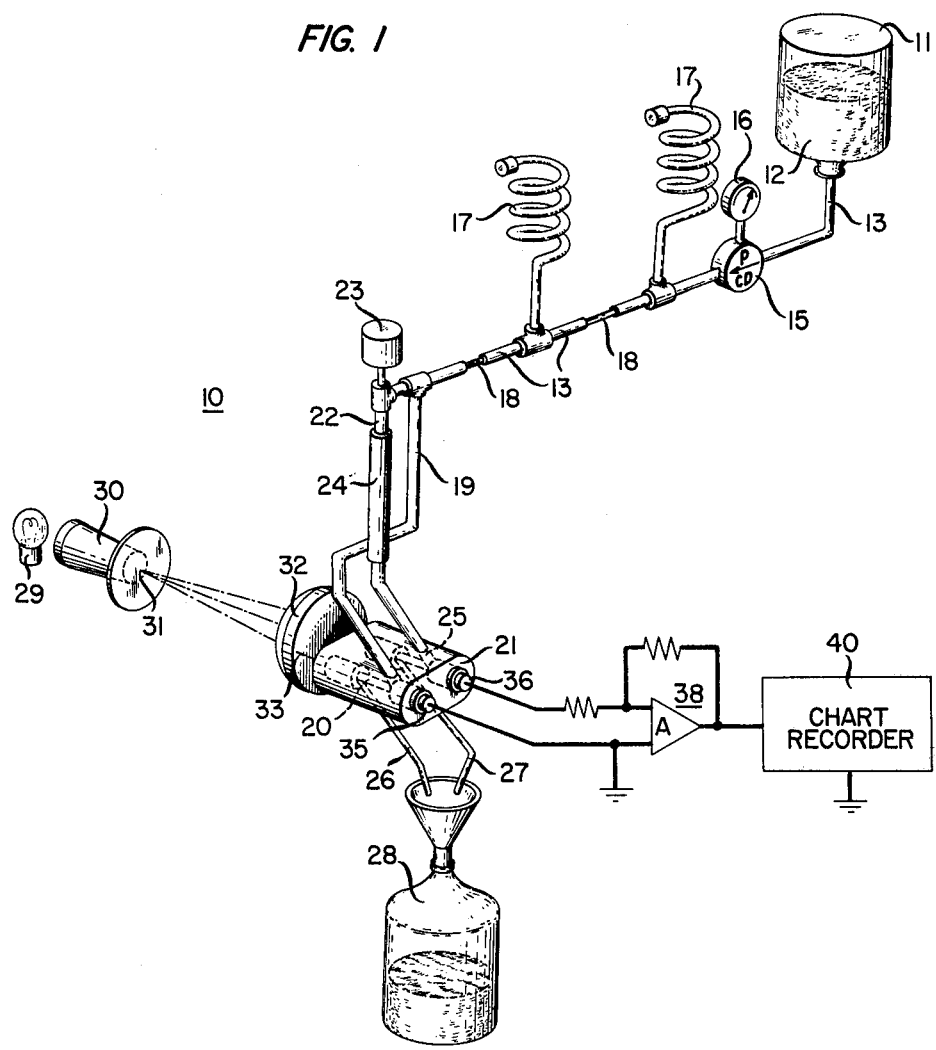
FIG. 1 is a schematic diagram of a liquid chromatography system arranged for utilizing a Christiansen effect detector in accordance with the invention.

Referring now to FIG. 1, there is shown a schematic diagram of a liquid chromatography system 10 using a double cell together with ancillary apparatus for determining refractive index variations caused by changes of the composition of the liquid, the apparatus utilizing Christiansen effects on light being transmitted through the cells.

The liquid separation portion of the system 10 is arranged generally in accordance with well known practice. A reservoir 11 stores a solvent liquid 12. Iso-octane is a suitable solvent liquid, or mobile phase, for circulating through the system as a carrier liquid. Tubing 13 transports the liquid 12 from the reservoir 11 to a pump 15 which forces the solvent to flow through the rest of the system 10 during operation. The pump 15 may be a reciprocating piston type which delivers a constant volume of liquid. This type of pump requires the use of damping devices for reducing pressure fluctuations to a negligible level. One method of dampening such fluctuations is by the use of a flow resistive network including accumulators 17 and restrictors 18 for smoothing out any pressure undulations that may occur. A pressure gauge 16 measures what pressure is being applied to the chromatography system.

After the solvent flows out of the accumulators and restrictors, the tubing separates into two branch tubes. A first branch tube 19 carries a portion of the solvent liquid through a first, or reference, cell 20 in a double cell apparatus 21. A second branch tube 22 carries the balance of the solvent liquid past a sample insertion septum 23, through a stationary phase column 24, and a second, or sample, cell 25 in the double cell apparatus 21. Liquid flowing out of the reference and sample cells 20 and 25 is carried respectively through output tubes 26 and 27 into a waste reservoir 28.

When the system is set up for testing a sample, collimated light is directed through the reference and sample cells. A source of light, such as an incandescent light bulb 29, shines a beam through a lens 30, a pinhole aperture 31, and a collimating lens 32 towards the cells 20 and 25. The wavelength of the light may be selected from a wide range of the spectrum of electromagnetic radiation including at least the ultraviolet and infrared spectra as well as the visible light spectrum. The bandwidth of light may be either narrow band or wide band. Collimating lens 32 may be either a single achromatic plano-convex lens or any known combination of lenses which will collimate light shining through the aperture 31. Such aperture is positioned at the focal point of the collimating lens 32 so that parallel rays of light 33 are directed along the lines of the center axes of the reference and sample cells 20 and 25. Some of the light impinging on each cell is transmitted therethrough respectively to light sensitive, or photodetector, circuits 35 and 36. Outputs of the photodetectors are amplified by an operational amplifier circuit 38 that is arranged to drive a printing strip-chart recorder 40 for providing a record of results of tests performed on samples injected into the system 10 at the septum 23.

Figure 2:
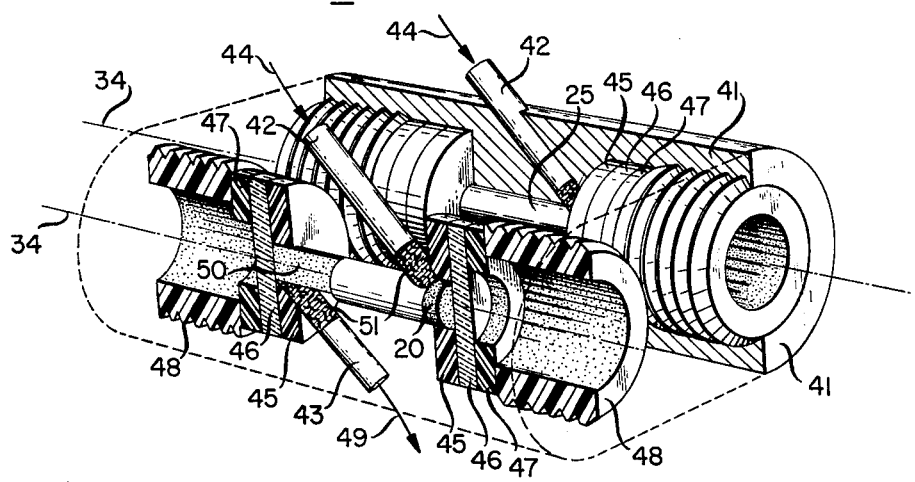
FIG. 2 is a cutaway perspective view of a double detector cell used in the system of FIG. 1.

Referring now to FIG. 2, there is shown the double cell aparatus 21 of FIG. 1. In FIG. 2 a body 41 forms the exterior and the principal structural member of the cell. This body doubles as a heat exchanger for maintaining both of the cells 20 and 25 at a common ambient temperature for purposes to be described more fully hereinafter. The body 41 may be fabricated out of any material having good heat conductivity, strength, and fabrication characteristics.

Inside of the body 41 are the two cylindrically shaped cells 20 and 25 having substantially parallel center axes 34. The cylinders for both cells are drilled completely through the body 41. The cells should be approximately equal in diameter and approximately equal in length from end to end. In one working model of the apparatus 21, the diameter of the cells is approximately 1.5 millimeters and the length of the cells is approximately 2.0 centimeters. An input port 42 and an output port 43 are drilled from the outside surface of the body 41 into each of the cells. The input ports 42 each intersect with a different one of the cells at or near the righthand end of that cell. The output ports 43 each intersect with a different one of the cells at or near the lefthand end of that cell. The inlet and outlet ports may be drilled at any angle into the cell wall, however, by drilling the ports at an acute angle with the cell wall one may enhance purging of the cell and reduce dead volume in accordance with standard practice.

Each of the cells 20 and 25 is confined at the righthand and lefthand ends by similar arrangements. A washer-shaped gasket 45 is inserted so that it lies perpendicular to the center axis 34 of the cell and so that its center hole is aligned with the cylindrical wall of the cell. A transparent flat glass, or quartz, disc 46 is inserted flush against the gasket 45 to lie also in a plane perpendicular to the center axis 34. The gasket 45 cushions the transparent disc 46 from the body 41 and together with the transparent disc 46 seals the end of the cell. Another washer-shaped gasket 47 is inserted flush against the outside surface of the transparent disc 46. The inside diameter of the gasket 47 should be large enough so that light can readily pass therethrough into or out of the cell. The outside diameter of the gaskets 45 and 47 should be substantially the same as an enlarged concentric access hole drilled from the end of the body 41 into the end of the cell. Gasket 45, transparent disc 46, and gasket 47 are held in place by a threaded bushing 48 which is screwed into the cell body 41 so that it fits snugly against the gasket 47. The photodetectors 35 and 36 of FIG. 1 are positioned either directly inside of or slightly outside of the bushing 48 depending on the focal length of the detector. The photodetectors 35 and 36 are located along the center axes 34 in such a manner that light emerging from the cell impinges on the photodetector circuitry and that any extraneous light sources are blocked from impinging upon photodetector circuitry.

Both of the input ports 42 and both of the output ports 43 intersect with the cylindrical cells so that continuous passages are available for the reference liquid to flow into the ports 42, as indicated by arrows 44, through the cells 20 and 25, and out of the ports 43, as indicated by arrow 49. Such flow paths through the cells 20 and 25 were previously mentioned in the description of FIG. 1.

Referring once again to FIG. 2, there is shown a dotted substance 50 filling the cells 20 and 25. This substance 50 is particulate matter that is confined to the cell by the gaskets 45 and 47, the transparent flat discs 46, and by porous plugs 51 inserted into the ports 42 and 43. The particulate matter and the porous plugs are selected so that the flow of liquid is restricted very little while passing through the cell. The porous plugs must, however, prevent the particulate matter from moving out of the cell. Such plugs 51 are not required if the inside diameter of the inlet and outlet tubes is smaller than the particle size of the particulate matter.

The size of the particles of the substance should be relatively uniform and may be any of a wide range of sizes but greater than the wavelength of light used. Good results have been achieved with a working model using particles of 20–40 mesh size.

In addition to the grain size, there are other factors which guide the selection of the particulate matter filling the cell. Many types of isotropic particles, such as solids, amorphous material, organic compounds, and inorganic substances can be used. The particles are selected to have a refractive index that is approximately equal to the refractive index of the solvent liquid. Such refractive indices generally are known and published for the sodium D-line. Lithium fluoride is a solid having a refractive index equal in magnitude to the magnitude of the refractive index of iso-octane at the sodium D-line and therefore is useful in the illustrative example. Because the refractive indices of lithium fluoride and iso-octane are very close, because iso-octane is a solvent for many possible samples, and because lithium fluoride is insoluble in iso-octane and has a lower value of dispersion than iso-octane, particles of lithium fluoride are suitable for use in the cells of a system utilizing iso-octane as the solvent liquid.

Although for convenience the refractive indices of the reference liquid and the solid particles can be closely matched at the wavelength of the sodium D-line, it is only necessary that the refractive indices of the solvent liquid and the particles be equal to one another at some specific wavelength within or near the spectrum common to the light source and the photodetectors. Many combinations of solvent liquids and solid particles or other particles can be selected from widely published index of refraction tables. Additional combinations can be made by adjusting the index of refraction of the solvent liquid. Such an adjustment of the index of refraction is accomplished by mixing two liquids having different refractive indices but similar solvent characteristics. Iso-octane and hexane are two liquids which have similar solvent characteristics but different refractive indices and therefore can be mixed to achieve an adjusted refractive index.

When the solvent liquid passes through the cell, the particulate matter is fully immersed in and wetted by the liquid.

As previously mentioned in reference to FIG. 1, collimated light is directed normal to the input transparent disc of each cell and parallel with the axis of each cell during operation of the apparatus 10. Because the refractive indices of the solvent liquid and the particulate matter are matched at the specific wavelength in the spectrum of interest, the particulate matter is transparent so that energy of such wavelength is transmitted undeviated through the cell. Energy having a wavelength other than the specific wavelength is deviated in accordance with the Christiansen effect.

Figure 3:
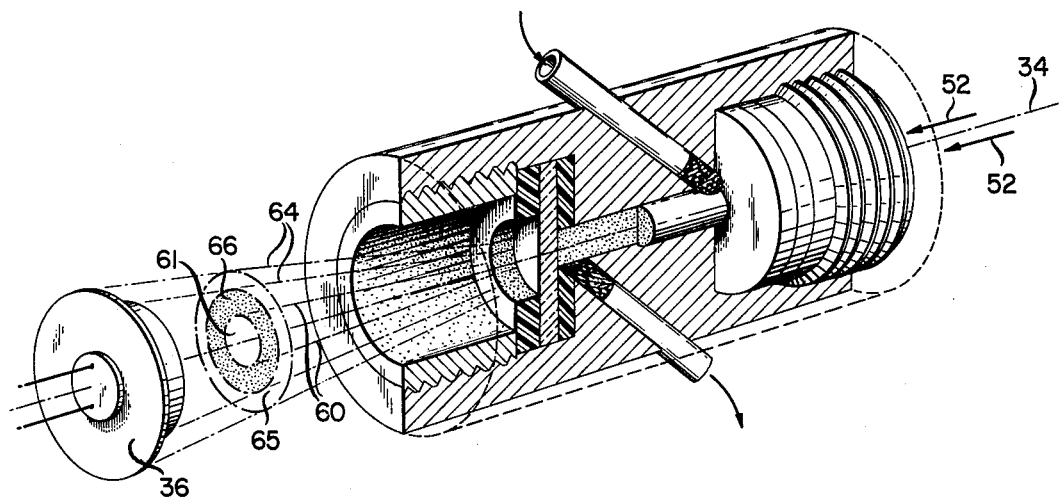
FIG. 3 is a cutaway perspective view of a cell showing operation of the cell in accordance with the invention.
Figure 4:
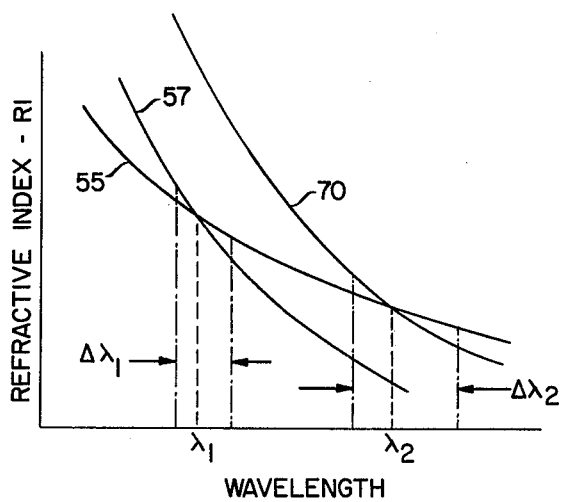
FIG. 4 is a graph of refractive index vs. wavelength.

Transmission of light through the cell may be better understood be reference to FIGS. 3 and 4 which show the Christiansen effect of the cell on an incident beam of collimated light 52. Such incident beam of light has either a narrow or a wide bandwidth substantially centered at the specific wavelength.

FIG. 4 shows a curve 55 representing refractive index versus wavelength for the solid particles of lithium fluoride in the cell 20. In the curve 55, refractive index slopes down from the shorter wavelengths to the longer wavelengths. A similar curve 57 representing the solvent liquid, iso-octane, has a greater downward slope than the slope of curve 55. Because of the difference in slopes of the two curves 55 and 57, these curves intersect at the specific, or predetermined, wavelength $\lambda_1$.

All light beam of 52, having a wavelength equal to the specific wavelength $\lambda_1$ and being normally incident to the transparent disc of the cell 20, is transmitted undeviated through the cell. In addition any incident light having a wavelength within a narrow band $\Delta\lambda_1$ is transmitted with little deviation through the cell. When such light within the band $\Delta\lambda_1$ emerges from the cell, a conically shaped center beam 60 is formed. This beam forms a spot 61 centered on the axis 34 of the cell. It is believed that most of the light in the center beam has a wavelength very close to the specific wavelength $\lambda_1$.

Any other light incident to the cell but having a wavelength other than within the band $\Delta\lambda_1$ is reflected, refracted, or scattered so much that it is absorbed on the cell walls or is deviated suffficiently from parallel with the center axis of the cell that it projects a conically shaped beam 64 forming a halo 65, as it emerges from the cell.

Intensity of the light transmitted through an arrangement like the cell of FIG. 3 is discussed at length in an article by Sethi, N.K. "On Wave-Propagation in Optically Heterogeneous Media, and the Phenomena Observed in Christiansen's Experiment", *Proceeding of the Indian Association for the Cultivation of Science,* 1921, pp. 121-141 and in another article by McAlister, E.D., "The Christiansen Light Filter: Its Advantages and Limitations", *Smithsonian Miscellaneous Collections,* 93, No. 7, Apr. 2, 1935. The foregoing references may aid the reader in understanding the phenomena occurring within the cell, but the reader must understand that the references discuss the Christiansen effect with respect to filters and that some of the material presented therein may not be directly applicable to the operation of cells arranged in accordance with the present invention.

In the cells 20 and 25 of FIG. 1, it is noted that the length of the cells and that the particle size remain constant once the cells are fabricated. The wavelength upon which the apparatus operates can be varied readily. Recall that the curve 57 of FIG. 4 represents the solvent liquid 12 of FIG. 1 and that curve 55 represents the solid particles in the cells 20 and 25. Bandwidth $\Delta\lambda_1$ is transmitted through both cells as long as the solvent liquid flows therethrough. However, when a sample is introduced into the apparatus 10 by way of the septum 23, it changes the composition of the liquid flowing to the cell 25. The solution of the sample in the solvent 12 has a refractive index versus wavelength curve 70 that moves away from the curve 57. Curve 70 is substantially parallel to but displaced vertically above curve 57. It is noted, however, that the curve 70 is parallel to the curve 57 only when the curve 70 has the same dispersion as the solvent of the curve 57. Although not shown in the drawing, it is noted that the curve 70 may be displaced vertically below the curve 57.

Curve 70 intersects the curve 55 at a different wavelength $\lambda_2$ where the refractive indices of the solid particles of lithium fluoride and of the solvent liquid containing the sample are equal. Light of wavelength $\lambda_2$ and of wavelengths within a narrow band $\Delta\lambda_2$ are transmitted through the cell 25 and project a pattern somewhat similar to the pattern projected from the cell 20.

FIG. 4 shows a graphic illustration of a sample being run through the sample cell 25 while the solvent liquid alone flows through the reference cell 20. The picture of FIG. 4, however, is no more than a snapshot taken of a dynamic operation. Actually when the solution containing the sample first enters the cell 25, the refractive index curve 70 begins to slide away from the curve 57. It continues sliding away from the curve 57 until it reaches a peak displacement. Thereafter it returns to the position of the curve 57 after all of the solution containing the sample leaves the cell 25.

Total intensity of the light transmitted through each cell is the integral of the intensities for all wavelengths within the bandwidth of transmitted light. The intensity determined for each wavelength is at least partly a function of the photodetector characteristics which may produce a higher output for longer wavelengths.

The bandwidth $\Delta\lambda_1$ transmitted through the reference cell depends upon the difference between the slopes of the curves 55 and 57. Likewise the bandwidth $\Delta\lambda_2$ transmitted through the sample cell 25 depends upon the difference between the slopes of the curves 55 and 70. Such slopes are the dispersions of the respective substances. Total intensity has been found to vary directly with wavelength so that longer wavelengths are transmitted with greater total intensity than shorter wavelengths.

Figure 5:
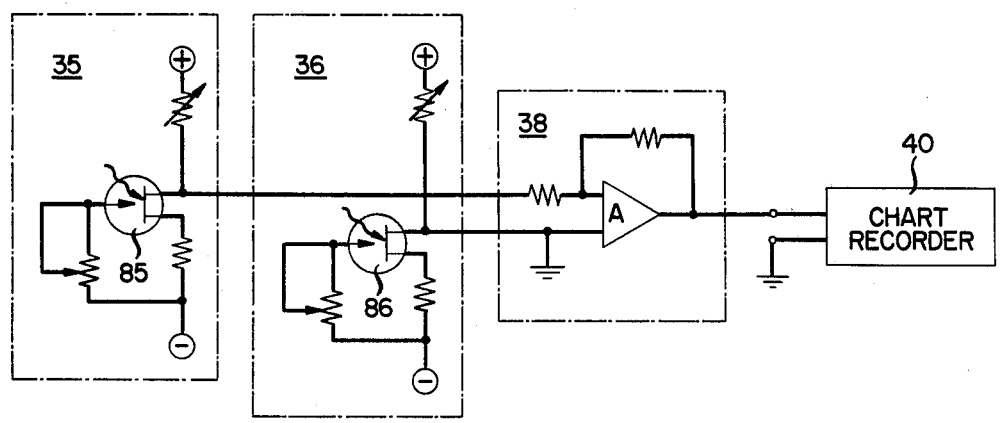
FIG. 5 is a schematic diagram of photodetector and amplifier circuitry for supplying signals to recording apparatus in accordance with FIG. 1.

Referring now to FIG. 5, there is shown separate circuits 35 and 36, respectively, for detecting the intensity of light transmitted through the cells 20 and 25. Light-sensitive field-effect transistor (photo FET) devices 85 and 86 included within the circuits are arranged to drive the operational amplifier 38. The photo FET devices are each housed in a cannister with a window at the top so that the cannister can be located in a position where light leaving the cell can impinge upon the light sensitive devices. The cannister should be positioned to receive optimum light being transmitted while extraneous sources of light are screened out as mentioned previously. The operational amplifier 38 may be any well known amplifier arrangement providing precise, low level signal amplification, low noise, low drift, and accurate closed loop gain.

A typical solution containing a sample in the solvent within the sample cell will transmit a greater intensity of light than the solvent alone in the reference cell. Some solutions containing a sample will reduce the intensity of light transmitted through the sample cell with respect to the light transmitted through the reference cell. In either case, the difference between the intensities is determined by the amplifier 38 and is printed on a chart by the recorder 40. By analyzing peaks shown on the resulting strip chart, an operator can determine what compounds are contained in the sample because different compounds require periods of time flow through the column 24, shown in FIG. 1.

Although the foregoing description has been presented with a reference cell and a sample cell, it is necessary to utilize only the sample cell while the reference cell is replaced by any reference device that will transmit a specific intensity of light. Light emerging from the sample cell and from the reference device is compared as described previously with respect to FIG. 5.

As shown by the different distances measured along the vertical axis of FIG. 4, the difference between intensities transmitted through the reference and through the sample cell can determine a difference in refractive index between the solvent and the sample in solution. The chart of the recorder must be calibrated for thus determining the difference in refractive index.

Referring once again to FIG. 3 there is shown only a single cell, which is similar to one side of the cell shown in FIG. 2. Such a single cell can be used in an arrangement like FIG. 1 but care must be taken to maintain the two cells at the same temperature.

As previously mentioned in the discussion of FIG. 2, the cells are sensitive to differences in temperature. This sensitivity to temperature is related to the fact that the refractive index of a liquid is a function of temperature. In fact the cells are so temperature dependent that any difference of temperature between the cells may be mistaken for a change of composition of the liquid in the sample cell. Therefore the reference and sample cells are kept at the same ambient temperature to minimize any fluctuation of light transmission resulting from temperature changes. Only fluctuations of light intensity caused by the change of composition in the sample cell as compared with the reference device are to be detected. Common fluctuations of light intensity caused by any change of temperature of the reference device and sample cell are rejected by the amplifier 38 of FIG. 5.

If for any reason the temperature effects on the readings remain too great for the accuracy required, the cells can be heated by a precisely controlled heat source for stabilizing the temperature of the cells and thereby further reducing fluctuations of light intensity caused by temperature.

The single cell of FIG. 2 may also be used to detect changes in the composition of a liquid flowing therethrough without the aid of a reference. Such an arrangement can detect variations in the composition of the liquid but such an arrangement has less stability than the dual arrangement of FIG. 1.

The foregoing discussion describes the basic configuration and operation of apparatus arranged in accordance with the invention. Broader aspects of the invention may be better understood by consideration of the following modifications which can be incorporated into the basic configuration.

As mentioned in the foregoing discussion, the photodetectors are positioned so that the center beams emerging from the cells impinge on the light sensitive devices. Such positioning of the devices is not necessarily essential. Instead they can be positioned to detect the intensity of light in the halo.

Figure 6:
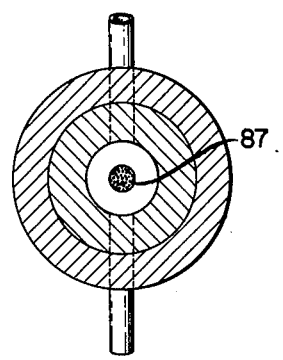
FIG. 6 is an end view of a cell in accordance with FIG. 3.

Referring now to FIG. 6, there is shown an end view of an alternative cell arranged to facilitate detection of the light in the halo. It is noted that an opaque spot 87 covers the center beam area of the cell for blocking the center beam from leaving the cell. This spot can be fixed to either end of the cell by any known method. By so blocking the center beam and by offsetting the photodetectors into the beam of the halo, the intensity of light in the halo can be detected.

Alternatively, an opaque cylinder can be positioned so that its axis is aligned with the axis of the cell. Light then is transmitted through a circular band of particulate matter and liquid surrounding the opaque cylinder. As transmitted light emerges from the cell, part of the halo will be projected along the axis of the cell where the photodetector ordinarily is placed.

The cross-section of the cell does not necessarily have to be circular. Any convenient cross-section can be used in the cell. A cell having a rectangular cross-section advantageously can be aligned with the filament of any light source having a straight filament.

The body 41 can be fabricated out of transparent material so that light, deviated sufficiently inside of the cell to impinge upon the walls of the cell at an angle within the critical angle of the material, is transmitted through the wall and is lost outside of the cell. Some transparent materials, such as glass, may have a heat conductivity that is less than the heat conductivity of some good conductors. The typical heat conductivity of glass, however, is sufficiently high to maintain the two cells at the same temperature.

The interior wall of the cell can be cut with substantially annular rings, such as buttress type threads, to help prevent deviated light from leaving the end of the cell and thereby prevent some light from impinging upon the photodetector.

It is noted that monochromatic light can be used for operating the apparatus. When monochromatic light is used, the specific wavelength of that light may be fixed. Therefore the particulate matter and the solvent liquid must be selected to have substantially equal refractive indices at that wavelength. The refractive index of the solvent can be adjusted by the addition of some suitable second solvent liquid to achieve the matching refractive indices at the desired specific wavelength, as previously described.

The above-detailed description is illustrative of several embodiments of the invention. It is understood that additional embodiments thereof will be obvious to those skilled in the art. All of the aforementioned embodiments are considered to be within the scope of the invention.

What is claimed is

1. A Christiansen effect detector comprising means for directing collimated light along a line through particulate matter immersed in a liquid, means for detecting intensity of the light transmitted through the matter and the liquid, cell means filled with the particulate matter and arranged for retaining the particulate matter and the liquid in a fixed length along the line of light wherein light emerging from the cell means forms a center beam and a halo, said detecting means positioned to determine intensity of light in the halo, means for blocking the center beam from impinging upon the detecting means, and means for flowing the liquid through the cell.

* * * * *